United States Patent [19]

Robson et al.

[11] Patent Number: 4,551,566

[45] Date of Patent: Nov. 5, 1985

[54] PROCESS FOR THE PRODUCTION OF ALKYLENE GLYCOLS

[75] Inventors: John H. Robson, Charleston; George E. Keller, II, S. Charleston, both of W. Va.

[73] Assignee: Union Carbide Corporation, Danbury, Conn.

[21] Appl. No.: 530,235

[22] Filed: Sep. 8, 1983

Related U.S. Application Data

[63] Continuation-in-part of Ser. No. 428,815, Sep. 30, 1982, abandoned.

[51] Int. Cl.[4] ...................... C07C 29/10; C07C 33/26; C07C 35/14; C07C 31/20
[52] U.S. Cl. .................................. 568/867; 568/700; 568/807; 568/811; 568/816; 568/833; 568/839; 568/857
[58] Field of Search ............... 568/700, 807, 811, 816, 568/833, 839, 857, 867

[56] References Cited

U.S. PATENT DOCUMENTS

| 2,141,443 | 12/1938 | Stanley et al. | 568/867 |
| 3,071,601 | 1/1963 | Aries | 568/867 |
| 4,277,632 | 7/1981 | Kumazawa et al. | 568/867 |

FOREIGN PATENT DOCUMENTS

| 73035 | 6/1981 | Japan | 568/867 |
| 2083026 | 3/1982 | United Kingdom | 568/867 |

Primary Examiner—J. E. Evans
Attorney, Agent, or Firm—Norman L. Balmer

[57] ABSTRACT

The process for the liquid-phase hydration of a vicinal alkylene oxide(s) to the corresponding alkylene glycol(s) comprising carrying out such hydration in the presence of a vanadate salt wherein the pH of the liquid phase is between about 5 and 12.

29 Claims, No Drawings

PROCESS FOR THE PRODUCTION OF ALKYLENE GLYCOLS

This is a continuation-in-part of U.S. Pat. No. 428,815, filed Sept. 30, 1982, now abandoned, herein incorporated by reference.

TECHNICAL FIELD

This invention relates to processes for the hydrolysis of vicinal alkylene oxides to the corresponding alkylene glycols. More specifically, it relates to processes for the production of alkylene glycols by the hydration of alkylene oxides in the presence of a water-soluble vanadate salt in a liquid menstruum having a pH of between about 5 to 12. Preferably, the vanadate salt comprises metavanadate salt.

BACKGROUND OF THE INVENTION

Alkylene oxides, for example ethylene oxide, propylene oxide and butylene oxide, have been subjected to liquid-phase hydration to produce the corresponding alkylene glycols. Commercially, in the production of ethylene glycol from ethylene oxide large molar excesses of water are used (See: Kirk-Othmer: Encyclopedia of Chemical Technology Volume 11, Third Edition, Page 939, (1980)). It has been reported that the presence of large quantities of water in the reaction system are necessary if the yield to the desired monoalkylene glycol is to be great enough to be commercially viable and minimize the production of by-products such as diglycols and triglycols. Accordingly, the commercial practice has generally involved the hydration of an alkylene oxide at a temperature of about 100° C. to about 200° C. in the presence of a large molar excess of water, for example, in excess of 15 moles of water per mole of alkylene oxide, when the corresponding monoalkylene glycol is to be produced. Unfortunately, the use of such large excesses of water presents significant energy and equipment requirements for its removal.

Since the selectivity of the hydration process to monoglycol, e.g., ethylene glycol, propylene glycol or butylene glycol, is dependent on the by-products formed, it would be desirable to provide a process that would increase the selectivity of the hydration process to monoglycol products. In addition, any process which would favorably decrease the relative amount of water employed to alkylene oxide hydrated while not increasing, or preferably decreasing, the by-products formed would be advantageous. Thus, the energy and equipment requirements would necessarily be less for separation and purification processes relating to the removal and recovery of the monoglycol from water and by-products.

As a result of the desire to improve the hydration process, both in terms of selectivity to desired product and the energy requirements to effect the purification and recovery of the desired product, several processes have been suggested which provide for the hydration of an alkylene oxide in the presence of a specific catalyst such that the ratio of water to alkylene oxide may be lowered and such that the selectivity to monoglycol product is maintained or enhanced.

Numerous catalysts have been suggested for use in the hydration of alkylene oxides, including the use of acid catalysts such as: alkyl sulfonic acid ion exchange resins (U.S. Pat. No. 4,165,440); carboxylic acids and halogen acids (U.S. Pat. No. 4,112,054); strong acid cation exchange resins (U.S. Pat. No. 4,107,221); aliphatic monocarboxylic and/or polycarboxylic acids (U.S. Pat. No. 3,933,923); cationic exchange resins (U.S. Pat. No. 3,062,889); acidic zeolites (U.S. Pat. No. 3,028,434); sulfur dioxide (U.S. Pat. No. 2,807,651); $Ca_3(PO_4)_2$ (U.S. Pat. No. 2,770,656); high-melting polyvalent metal fluorides (U.S. Pat. No. 2,547,766); trihalogen acetic acid (U.S. Pat. No. 2,472,417); and copper-promoted aluminum phosphate (U.S. Pat. No. 4,014,945).

In addition to the acid catalysts, numerous catalysts have been suggested for the hydration of alkylene oxides in the presence of carbon dioxide. These include alkali metal halides, such as chlorides, bromides and iodides, quaternary ammonium halides such as tetramethyl ammonium iodide and tetramethyl ammonium bromide (British Pat. No. 1,177,877); organic tertiary amines such as triethylamine and pyridine (German published patent application No. 2,615,595, Oct. 14, 1976, and U.S. Pat. No. 4,307,256, issued Dec. 22, 1981); quaternary phosphonium salts (U.S. Pat. No. 4,160,116, issued July 3, 1979); and chlorine or iodine-type anion exchange resins (Japanese Kokai No. 57/139,026, published Aug. 27, 1982); and partially amine-neutralized sulfonic acid catalyst, e.g., partially amine-neutralized sulfonic acid resin (U.S. Pat. No. 4,393,254, issued July 12, 1983).

Although a review of the results reported in the patent literature would suggest that the above described catalysts have provided commercially acceptable results, that is, a high selectivity to the monoglycol product and a decrease in the requirement for large molar excess of water, these catalysts have not been commercially employed for several reasons. For example, alkali metal halides tend to corrode the reaction system at the temperatures employed for the hydration of alkylene oxides. The relatively low solubility of alkali metal halides and quaternary ammonium halides in alkylene glycol restricts their use as hydration catalysts since they are likely to precipitate within the reaction system during the course of the hydration reaction and can result in problems associated with cleaning the reaction system. In addition, some catalysts, such as tertiary amines, have certain chemical and physical properties which prevent their ready use as hydration catalysts. For example, tertiary amines have a strong pungent odor which is not desirable in manufacturing and can detract from the quality of the end product.

U.S. Pat. No. 4,277,632, issued July 7, 1981, discloses a process for the production of alkylene glycols by the hydrolysis of alkylene oxides in the presence of a catalyst of at least one member selected from the group consisting of molybdenum and tungsten. The patent discloses that the catalyst may be metallic molybdenum or metallic tungsten, or inorganic or organic compounds thereof, such as oxides, acids, halides, phosphorous compounds, polyacids, alkali metal and alkaline earth metal, ammonium salts and heavy metal salts of acids and polyacids, and organic acid salts. An objective of the disclosed process is stated to be the hydrolysis of alkylene oxides wherein water is present in about one to five times the stoichiometric value without forming appreciable amounts of by-products, such as the polyglycols. The reaction may be carried out in the presence of carbon dioxide; however, when the reaction is carried out in the presence of nitrogen, air, etc. the patentees state that the pH of the reaction mixture should be adjusted to a value in the range of 5 to 10.

Japanese Kokai No. JA 54/128,507, published Oct. 5, 1979, discloses a process for the production of alkylene glycols from alkylene oxides and water using metallic tungsten and/or tungsten compounds.

Japanese Kokai No. JA 56/073,035, published June 17, 1981, discloses a process for the hydrolysis of alkylene oxide under a carbon dioxide atmosphere in the presence of a catalyst consisting of a compound containing at least one element selected from the group of titanium, zirconium, vanadium, niobium, tantalum and chromium. The compounds include the oxides, sulfides, acids, halides, phosphorous compounds, polyacids, alkali metal salts of acids and polyacids, ammonium salts of acids and polyacids, and heavy metal salts of acids. Although the examples show the use of various metal catalysts, the disclosure does not disclose any detail as to the nature of the hydration process and the selection of the catalysts employed therein. In example 2, the process is carried out using a potassium vanadate as the hydration catalyst for the production of ethylene glycol from ethylene oxide and water under a carbon dioxide pressure. No identification of the vanadate used was made. The conversion of ethylene oxide to products is reported to be 100 percent but the selectivity to monoethylene glycol is only 50 percent. The combined selectivity to diethylene glycol and triethylene glycol is also 50 percent. Thus, example 2 shows that the use of potassium vanadate was only slightly better than the obtained 36.1 percent selectivity reported for the conversion of ethylene oxide to ethylene glycol wherein no catalyst was employed, (see comparative example 1 of No. JA 56/073,035), and suggests that potassium orthovanadate was employed. In addition, a process wherein the selectivity to monoethylene glycol is greater than 70 molar percent is not disclosed.

Japanese Kokai No. JA 56/073,036, published June 17, 1981, discloses a process for the hydrolysis of alkylene oxide under a carbon dioxide atmosphere in the presence of a catalyst consisting of a compound containing at least one element selected from a group comprising aluminum, silicon, germanium, tin, lead, iron, cobalt and nickel.

OVERVIEW OF THE INVENTION

This invention relates to processes for the production of the corresponding monoalkylene glycol by the hydration in a liquid phase of an alkylene oxide having the general formula:

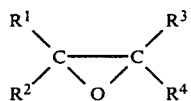

$R^1$, $R^2$, $R^3$ and $R^4$ being as hereinafter set forth, in the presence of a water-soluble vanadate salt.

In accordance with an aspect of this invention, the liquid phase has a pH of between about 5 and about 12. Advantageously, the vanadate salt comprises metavanadate.

The processes of this invention provide enhanced selectivity to monoalkylene glycol. For instance, the selectivities achievable using this invention are greater than those obtained under common conditions but not employing a vanadate salt or those obtained under common conditions including using a vanadate salt but not at a pH in accordance with the invention.

DETAILED DESCRIPTION OF THE INVENTION

This invention relates to processes for the production of monoalkylene glycols by the reaction of water with vicinal alkylene oxide having the general formula

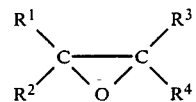

wherein $R^1$, $R^2$, $R^3$ and $R^4$ each designate a hydrogen atom, an alkyl group having between 1 and about 10 carbon atoms, an aryl group having at least 6 carbon atoms (e.g., monocyclic or bicyclic aryl), an alkenyl group having 2 or 3 carbon atoms or a cycloalkyl group having 3 to 6 carbon atoms. Representative of the alkylene oxides which may be employed in the instant invention are ethylene oxide, propylene oxide, butylene oxides, including isobutylene oxide, 1,2-butylene oxide and 2,3-butylene oxide, pentylene oxide, cyclohexene oxide, styrene oxide, and the like. Preferably, the alkylene oxide is an aliphatic oxide such as ethylene oxide and propylene oxide.

The source of the alkylene oxide is not generally important, and alkylene oxide formed by most any process may be employed in the instant invention. For example, if ethylene oxide is the selected alkylene oxide it may be formed by the catalytic oxidation of ethylene with molecular oxygen or an oxygen-containing gas in the presence of a silver catalyst. Such a process for forming the ethylene oxide employed herein is particularly desirable since substantially pure ethylene oxide may be obtained.

The process also employs water as a reagent for the formation of the corresponding alkylene glycol. The source of the water is not important. Demineralized water obtained by, for example, ion exchange treatment, or other water of sufficient purity is usable in hydration processes. The amount of water to be used, relative to a mole of alkylene oxide, is generally between about 1 and about 40 moles, preferably up to about 30 moles, say, between about 1 and 30 moles and preferably between about 1 and 20 moles, and about 1 to about 10 moles if reducing energy and equipment costs for glycol-water separation is a primary objective. Although the molar ratio of water required for hydrolysis to alkylene oxide may be decreased below about 5 moles of water per mole of alkylene oxide, it is generally desirable to maintain at least a slight molar excess of water over the stoichiometric amount of water to ensure a higher selectivity of alkylene oxide to the monoalkylene glycol product. Thus, by the use of the vanadate salt in accordance with this invention and the molar ratio of water to alkylene oxide (i.e., molar hydrolysis ratio), commercially attractive selectivities to monoalkylene glycol can be obtained, e.g., greater than about 70, say, greater than about 80, percent.

The processes of this invention employ a water-soluble vanadate salt containing a suitable cation. The vanadate anion employed is believed not important so long as it is capable of forming, or is, the metavanadate ion. While, in an aspect of this invention, the vanadate anion comprises metavanadate anion, other vanadate anions may be used in accordance with the broader aspects of this invention. Vanadate chemistry is complex and numerous vanadate anion species, e.g., metavanadate, pyrovanadate and orthovanadate anions, have been identified although their specific structures are not fully known. For purposes of discussion, common structural reference to these anions is as follows: metavanadate, $(VO_3)^-$; pyrovanadate, $(V_2O_7)^{4-}$; and orthovanadate, $(VO_4)^{3-}$. Intermediate vanadate anions may also exist such as $(HV_2O_7)^{3-}$. The particular vanadate species present is thought to be dependent on the pH of the liquid phase. Hence, at a pH of, say, about 12, little, if any, metavanadate anion may exist. Although the processes are carried out by providing a water-soluble vanadate salt to the reaction system, the exact nature of the catalytic species is not fully known.

The selection of the vanadate salt will in general be dependent on the water solubility of the selected vanadate salt compound. Cations which are believed to be acceptable as the counter ion to the vanadate anion are the alkali metals, the alkaline earth metals, quaternary ammonium cations, ammonium, copper, zinc, iron, and other cations which provide a water-soluble vanadate salt under the reaction conditions.

The vanadate may be used in the salt form or may be introduced into the reaction system on a support, such as on a carrier such as silica, alumina, zeolites, clay, and the like. When the process is carried out, the vanadate is generally in a dissolved, mixed, suspended, or deposited form in a fixed bed in the liquid phase with the reactants; i.e., the alkylene oxide and water. The vanadate may be provided to the reaction system by mixing it with water being introduced into the reaction system or it may be introduced by means of a separate inlet to the reaction system. The exact means of introduction of the vanadate is not critical, and frequently the vanadate is provided at the beginning of the reaction and/or is continuously or intermittently added at a fixed rate during the reaction.

The vanadate salt (calculated as metavanadate anion regardless of the form of the vanadate anion added to, or present in, the reaction system) is generally provided in an amount of at least 0.005 percent, based on the weight of the vicinal alkylene oxide employed, and is preferably employed in an amount between about 0.01 and about 90 percent by weight, and most preferably between about 0.05 and about 30 percent by weight, based on the weight of the alkylene oxide employed.

The production of alkylene glycol according to this invention is effectively carried out in the presence of a gas, such as air, carbon dioxide, argon, nitrogen, and the like, as a diluent for the reaction system. The very nature of the process generally provides carbon dioxide and nitrogen in the reaction system. The presence of carbon dioxide has been observed, in some instances, to decrease the selectivity to the monoethylene glycol product and, as a result, the presence of carbon dioxide is sometimes not preferred although some carbon dioxide will normally be present. In general, when the reaction is conducted under conditions in which substantially all of the vanadate anion is believed to be metavanadate anion, carbon dioxide is desirably present in an amount less than about 0.10 mole of carbon dioxide per mole of alkylene oxide present under the reaction conditions, preferably less than about 0.05 mole of carbon dioxide per mole of alkylene oxide.

By this invention, the adjustment of the pH of the reaction system can affect the rate and, importantly, selectivity to monoalkylene glycol. Although the exact relationship of selectivity and pH is not yet known, it is believed that, for instance, a metavanadate anion may undergo in situ modification to provide the catalytic species of vanadium which provides the advantageous selectivities to monoethylene glycol. In general, the initial pH of the reaction system is between about 5 and about 12, e.g., about 7 to 11, and preferably, the pH is within the ranges during the process. It is believed that the pH should be between about 7 and about 10.

The pH may be affected by a number of mechanisms. For instance, acid or base such as sulfuric acid, hydrochloric acid, phosphoric acid, carbonic acid, alkali metal hydroxide (e.g., sodium hydroxide and potassium hydroxide), ammonium hydroxide and the like may be added. Preferably, an adjuvant, which is used to modify the pH, does not result in precipitation of the vanadate or does not otherwise untowardly affect the reaction system or products. In many instances, the pH is affected by the vanadate salt added and its concentration. For example, orthovanadate is strongly basic and may be used in combination with metavanadate or pyrovanadate as a means to adjust the pH. Similarly, the concentration of vanadate salt will affect the pH.

The process is usually carried out at a temperature between about 20° C. and about 250° C., preferably between about 50° C. and about 200° C. Temperatures above 250° C. may be employed depending on the selection of the alkylene oxide, vanadate salt compound and pressure employed; however, such high temperatures are not generally preferred.

The process is typically carried out at a pressure in the range between about 0 kg/cm$^2$G and about 1000 kg/cm$^2$G and preferably between about 2 kg/cm$^2$G and about 100 kg/cm$^2$G, although pressures outside these preferred ranges are believed to be operable.

The process of this invention can be operated in the presence of a water-miscible solvent which may serve to dilute the reaction mixture. Any liquid which at the reaction temperature is totally miscible with the alkylene oxide water and the glycol product(s), can be a solvent; provided that it is not reactive with either the alkylene oxide reactant, the alkylene glycol produced or the vanadate salt employed. Thus, compounds such as carboxylic acid, phenols, aldehydes and alkylene carbonates are preferably not employed as solvents in the practice of this invention. The alkylene glycol product is often a very good solvent. If an alkylene glycol is employed as a solvent, preferably it is the same as the alkylene glycol product. The solvents are useful for the purpose of controlling reaction temperature (particularly at low hydrolysis ratios) and rate and are useful in recycle systems in continuous processes.

The processes of this invention may be carried out as a batch reaction or as a continuous process. Conventional autoclaves can be employed when using elevated temperatures, but glassware-type equipment can be used when operated at moderate pressures. Plug-flow reactors are often utilized in conventional continuous procedures. Solvent may be recycled and catalyst may be recovered.

The reaction may be carried out for very short periods of time, e.g., fractions of a second, and, if desired, may be carried out over reaction periods up to hours. The process conditions are governed by the amounts of solvent and catalyst employed, the pressures and temperatures employed, and like considerations.

It has been observed that when the alkylene oxide is ethylene oxide, the selectivity to monoethylene glycol over diethylene glycol and triethylene glycol is greater than 70 molar percent and generally greater than 80 molar percent.

As can be seen from this disclosure, the combinations of hydrolysis ratio, vanadate concentration, and pH can be correlated to provide optional results for a particular objective. For example, if the objective is to provide high selectivity to monoalkylene glycol, higher hydrolysis ratios may be employed, and selectivities of greater than 95 percent at 20:1 molar hydrolysis ratios may be achievable. If the objective is to use low hydrolysis ratios to reduce the costs associated with the glycol-water separation, the comparable selectivities to those obtained in conventional hydrolysis operations may be achievable at low hydrolysis ratios. For example, selectivities of greater than 90 percent can be obtained at molar hydrolysis ratios of around 5:1.

The following examples show various modes in the practice of this invention but are not intended to limit the invention. All parts and percentages of solids are by weight and of liquids and gases are by volume unless otherwise indicated.

EXAMPLES 1 TO 7

The examples were carried out with a stainless steel autoclave having an internal volume of about 300 cubic centimeters. Prior to the introduction of reactants to the autoclave, the autoclave was purged with nitrogen at ambient temperature (between about 18° C. and 22° C.). The reactants (e.g., ethylene oxide, water and sodium metavanadate) were introduced to the reactor at ambient temperature with stirring. The autoclave was heated to about 140° C. with stirring and maintained at 140° C. for a period of one hour. The autoclave and its contents were then cooled to ambient internal temperature, and the contents and standards were analyzed by standard vapor phase chromatographic techniques by employing a Varian 3700 TM gas chromatograph equipped with 1 meter × ⅛ inch (0.32 centimeters) (outside diameter) stainless steel column packed with a four percent Carbowax 20M TM on a 40/60 mesh Chromosorb T TM.

The results of examples 1 to 7 are set forth in Table I. The examples show that even with varying amounts of ethylene oxide and water the selectivity to ethylene glycol is 73 percent or higher when the metavanadate anion was present. Example 7 is a comparative example wherein no vanadate was employed.

TABLE I

| Example | Ethylene Oxide[1] | Water[1] | NaVO$_3$[1] | Ethylene Glycol[2] |
|---|---|---|---|---|
| 1 | 35.0 | 65.5 | 1.6 | 83 |
| 2 | 34.0 | 67.5 | 3.2 | 91 |
| 3 | 35.0 | 67.5 | 3.2 | 89 |
| 4 | 16.5 | 181.5 | 1.6 | 95 |
| 5 | 36.0 | 34.0 | 1.6 | 73 |
| 6 | 35.0 | 35.0 | 3.2 | 84 |
| 7 | 35.0 | 67.5 | — | 63 |

[1]amount given in grams
[2]Selectivity = $\frac{\text{Weight of Ethylene Glycol}}{\text{Weight of EG + DEG + TEG}} \times 100$
EG = Ethylene Glycol; DEG = Diethylene Glycol; and TEG = Triethylene Glycol

EXAMPLES 8 TO 11

Examples 8 to 11 were carried out in the same manner as examples 1 to 7 except that carbon dioxide was introduced to the autoclave and the amounts were as reported in Table II. The effect of carbon dioxide is surprising since JA 56/073035 teaches that the presence of carbon dioxide improves the selectivity to monoalkylene glycol. In contrast, examples 8 to 11 show that the selectivity to monoethylene glycol using metavanadate anion improves with a decrease in the presence of carbon dioxide. The results of examples 8 to 11 are set forth in Table II. Examples 8 and 10 are comparative examples.

TABLE II

| Example | Ethylene Oxide[1] | Water[1] | NaVO$_3$[1] | Carbon Dioxide[2] | Ethylene Glycol[3] |
|---|---|---|---|---|---|
| 8 | 35.0 | 67.5 | 3.2 | 100 | 82 |
| 9 | 35.0 | 67.5 | 3.2 | — | 89 |
| 10 | 33.0 | 33.0 | 3.2 | 100 | 68 |
| 11 | 35.0 | 35.0 | 3.2 | — | 84 |

[1]Amount given in grams (metavanadate as added to the liquid phase)
[2]Pressure in pounds per square inch gauge
[3]Selectivity calculated as in Table I

EXAMPLES 12 AND 13

Examples 12 and 13 are comparative examples and were carried out in the same manner as examples 1 to 7, except that sodium hydroxide and sodium orthovanadate were employed, respectively. Examples 12 and 13 show that the instant process is distinguished from a process employing the orthovanadate salt and from a process employing a strong base catalyst.

In example 12 an autoclave was charged with 67.5 grams of water and 35.0 grams of ethylene oxide and the pH of the resulting mixture adjusted to about 12.5 by addition of sodium hydroxide. In example 13 an autoclave was charged with 67.5 grams of water and 35.0 grams of ethylene oxide and 3.2 grams of sodium orthovanadate. The resulting mixtures had a pH of 12.5. The results of examples 12 and 13 are set forth in Table III.

TABLE III

| Example | Catalyst | EG[1] | DEG[1] | TEG[1,2] | Initial pH |
|---|---|---|---|---|---|
| 12 | NaOH | 26.2 | 34.6 | 39.2 | 12.5 |
| 13 | Sodium Orthovanadate | 32.5 | 32.2 | 35.2 | 12.5 |

[1]Selectivity = $\frac{\text{Weight of Product}}{\text{Weight of EG + DEG + TEG}}$
EG = Ethylene Glycol; DEG = Diethylene Glycol; and TEG = Triethylene Glycol
[2]Tetraethylene glycol was qualitively observed

EXAMPLES 14 TO 20

Examples 14 to 20 were carried out in the same manner as examples 1 to 7 except that the initial pH was adjusted with an aqueous sodium hydroxide solution or phosphoric acid. The details of the examples are reported in Table IV.

TABLE IV

| Example | Ethylene Oxide[1] | Water[1] | NaVO$_3$[1] | pH | EG[2] | DEG[2] | TEG[2] |
|---|---|---|---|---|---|---|---|
| 14 | 67.0 | 37.0 | 3.20 | 8.0[3] | 87.7 | 11.5 | 0.8 |
| 15 | 67.0 | 33.0 | 3.20 | 8.5[3] | 88.4 | 10.9 | 0.7 |
| 16 | 67.0 | 34.0 | 3.20 | 9.0[3] | 89.0 | 10.5 | 0.6 |
| 17 | 67.0 | 34.0 | 3.20 | 9.5[4] | 90.8 | 8.5 | 0.4 |
| 18 | 67.0 | 33.0 | 3.20 | 10.0[4] | 91.1 | 8.5 | 0.4 |
| 19 | 67.0 | 34.0 | 3.20 | 10.5[4] | 90.6 | 8.9 | 0.5 |

TABLE IV-continued

| Example | Ethylene Oxide[1] | Water[1] | NaVO$_3$[1] | pH | EG[2] | DEG[2] | TEG[2] |
|---|---|---|---|---|---|---|---|
| 20 | 67.0 | 35.0 | 3.20 | 11.0[4] | 85.4 | 13.2 | 1.4 |

[1] Amount given in grams (metavanadate as added to the liquid phase.)
[2] Selectivity = $\dfrac{\text{weight of product}}{\text{weight of EG + DEG + TEG}}$
EG = Ethylene Glycol; DEG = Diethylene Glycol; and TEG = Triethylene Glycol.
[3] pH adjustment using phosphoric acid.
[4] pH adjustment using sodium hydroxide solution.

Thus it can be seen that a pH of about 8 to 11 provides excellent results.

It is claimed:

1. A process for the production of monoalkylene glycol comprising reacting in a liquid phase, a vicinal alkylene oxide of the formula:

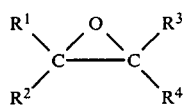

wherein $R^1$, $R^2$, $R^3$ and $R^4$ each designate a hydrogen atom, an alkyl group having between 1 and about 10 carbon atoms, an aryl group having at least 6 carbon atoms, an alkenyl group having 2 or 3 carbon atoms or a cycloalkyl group having 3 to 6 carbon atoms, with water in the presence of a sufficient amount of water-soluble vanadate salt to enhance the selectivity of the reaction to monoalkylene glycol, said liquid phase having a pH of between about 8 to 11.

2. The process of claim 1 wherein the molar ratio of water to alkylene oxide is less than about 30.

3. The process of claim 2 wherein the temperature of the reaction is between about 20° and 250° C.

4. The process of claim 2 wherein the pressure of the reaction is between about 0 kg/cm$^2$G and about 1000 kg/cm$^2$G.

5. The process of claim 2 wherein the pH and molar ratio of water to alkylene glycol are sufficient to provide a selectivity to monoalkylene glycol of at least about 80 percent.

6. The process of claim 5 wherein the pH and molar ratio of water to alkylene glycol are sufficient to provide a selectivity to monoalkylene glycol of at least about 90 percent.

7. The process of claim 1 wherein the molar ratio of water to alkylene oxide is about 1:1 to 10:1.

8. The process of claim 5 wherein the water-soluble vanadate comprises metavanadate.

9. The process of claim 5 wherein the water-soluble vanadate salt is an alkali metal salt.

10. The process of claim 1 wherein the alkylene glycol is ethylene glycol.

11. The process of claim 5 wherein the alkylene glycol is ethylene glycol.

12. The process for the production of monoalkylene glycols comprising the reaction of a vicinal alkylene oxide having the formula:

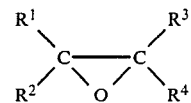

wherein $R^1$, $R^2$, $R^3$ and $R^4$ each designate a hydrogen atom, an alkyl group having between 1 and about 10 carbon atoms, an aryl group having at least 6 carbon atoms, an alkenyl group having 2 or 3 carbon atoms or a cycloalkyl group having 3 to 6 carbon atoms, with water in the presence of a water-soluble metavanadate.

13. The process of claim 12 wherein the molar ratio of water to alkylene oxide is between about 1 and about 40.

14. The process of claim 13 wherein the molar ratio of water to alkylene oxide is between about 1 and about 30.

15. The process of claim 14 wherein the molar ratio of water to alkylene oxide is between about 1 and about 10.

16. The process of claim 12 wherein the aklylene oxide is ethylene oxide.

17. The process of claim 12 wherein the alkylene oxide is propylene oxide.

18. The process of claim 12 wherein the alkylene oxide is a butylene oxide.

19. The process of claim 12 wherein the metavanadate is an alkali metal metavanadate.

20. The process of claim 19 wherein the metavanadate is sodium metavanadate.

21. The process of claim 19 wherein the metavanadate is potassium metavanadate.

22. The process of claim 19 wherein the amount of metavanadate is not less than 0.005 percent by weight based on the weight of alkylene oxide employed.

23. The process of claim 22 wherein the amount of metavanadate is between about 0.05 and about 30 percent by weight, based on the weight of alkylene oxide.

24. The process of claim 12 wherein the process is carried out in the presence of less than about 0.10 mole of carbon dioxide per mole of alkylene oxide.

25. The process of claim 24 wherein the process is carried out in the presence of less than about 0.05 mole of carbon dioxide per mole of alkylene oxide.

26. The process of claim 12 wherein the process is carried out at a temperature between about 20° C. and about 250° C.

27. The process of claim 12 wherein the pressure is between about 0 kg/cm$^2$G and about 1000 kg/cm$^2$G.

28. The process of claim 16 wherein the selectivity to monoethylene glycol is greater than 70 percent.

29. The process of claim 28 wherein the selectivity to monoethylene glycol is greater than 80 percent.

* * * * *